US010245365B2

(12) United States Patent
Gerber et al.

(10) Patent No.: US 10,245,365 B2
(45) Date of Patent: Apr. 2, 2019

(54) REPLENISIHING UREASE IN DIALYSIS SYSTEMS USING A UREASE INTRODUCER

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/003,245

(22) Filed: Jun. 8, 2018

(65) Prior Publication Data

US 2018/0289880 A1    Oct. 11, 2018

Related U.S. Application Data

(62) Division of application No. 14/633,852, filed on Feb. 27, 2015, now Pat. No. 10,016,553.

(60) Provisional application No. 62/077,167, filed on Nov. 7, 2014, provisional application No. 62/016,613, filed on Jun. 24, 2014.

(51) Int. Cl.
  *B01D 24/00*  (2006.01)
  *A61M 1/16*  (2006.01)
  *B01D 35/00*  (2006.01)

(52) U.S. Cl.
  CPC ................. *A61M 1/1696* (2013.01)

(58) Field of Classification Search
  CPC ...... B01D 24/00; B01D 24/001; B01D 24/10; B01D 24/105; B01D 24/04; B01D 24/4689; B01D 24/4694; B01D 35/00; B01D 35/12; B01D 35/30; B01D 2201/30; B01D 2201/301; B01D 2201/305

USPC ....... 210/234, 236, 263, 287, 291, 503, 638, 210/632, 633, 660, 662, 670, 749, 767, 210/792, 807, 282
See application file for complete search history.

(56) References Cited

U.S. PATENT DOCUMENTS 1,617,288 A    2/1927 Kenney
2,703,313 A *  3/1955 Gill .................. B01J 47/026
                                              210/120
3,608,729 A    9/1971 Haselden
(Continued)

FOREIGN PATENT DOCUMENTS

CN        1487853 A     4/2004
CN      103402563 A    11/2013
(Continued)

OTHER PUBLICATIONS

U.S. Appl. No. 14/637,606_OA.
(Continued)

*Primary Examiner* — Allison G Fitzsimmons
(74) *Attorney, Agent, or Firm* — Kenneth Collier; Roger Hahn

(57) ABSTRACT

An apparatus and method for replenishing urease in a sorbent cartridge for use in sorbent dialysis. The sorbent cartridge is configured to allow an amount of urease to be added to the sorbent cartridge. A urease solution can be injected into the sorbent cartridge to replenish the urease containing module, or solid urease can be added to the sorbent cartridge. The sorbent module can also comprise other, rechargeable, sorbent materials for removing toxins other than urea from spent dialysate.

23 Claims, 6 Drawing Sheets

(56) References Cited

U.S. PATENT DOCUMENTS

| | | | |
|---|---|---|---|
| 3,617,558 A | 11/1971 | Jones | |
| 3,669,880 A | 6/1972 | Marantz | |
| 3,776,819 A | 12/1973 | Williams | |
| 3,850,835 A | 11/1974 | Marantz | |
| 3,884,808 A | 5/1975 | Scott | |
| 3,902,490 A | 9/1975 | Jacobsen | |
| 3,989,622 A * | 11/1976 | Marantz | A61M 1/1696 210/645 |
| 4,073,725 A | 2/1978 | Takeuchi | |
| 4,094,775 A | 6/1978 | Mueller | |
| 4,206,054 A | 6/1980 | Moore | |
| 4,209,392 A | 6/1980 | Wallace | |
| 4,376,707 A | 3/1983 | Lehmann | |
| 4,460,555 A | 7/1984 | Thompson | |
| 4,581,141 A | 4/1986 | Ash | |
| 4,650,587 A | 3/1987 | Polak | |
| 4,661,246 A | 4/1987 | Ash | |
| 4,684,460 A | 8/1987 | Issautier | |
| 4,687,582 A | 8/1987 | Dixon | |
| 5,230,702 A | 7/1993 | Lindsay | |
| 5,284,470 A | 2/1994 | Beltz | |
| 5,302,288 A | 4/1994 | Meidl | |
| 5,308,315 A | 5/1994 | Khuri | |
| 5,507,723 A | 4/1996 | Keshaviah | |
| 5,662,806 A | 9/1997 | Keshaviah et al. | |
| 5,770,086 A | 6/1998 | Indriksons | |
| 5,849,179 A | 12/1998 | Emerson | |
| 5,858,186 A | 1/1999 | Glass | |
| 5,944,684 A | 8/1999 | Roberts | |
| 6,036,858 A | 3/2000 | Carlsson | |
| 6,114,176 A | 9/2000 | Edgson et al. | |
| 6,126,831 A | 10/2000 | Goldau | |
| 6,521,184 B1 | 2/2003 | Edgson et al. | |
| 6,572,769 B2 | 6/2003 | Rajan | |
| 6,579,460 B1 | 6/2003 | Willis | |
| 6,627,164 B1 | 9/2003 | Wong | |
| 6,666,840 B1 | 12/2003 | Falkvall et al. | |
| 6,719,745 B1 | 4/2004 | Taylor | |
| 6,814,724 B2 | 11/2004 | Taylor | |
| 6,818,196 B2 | 11/2004 | Wong | |
| 6,861,266 B1 | 3/2005 | Sternby | |
| 6,878,258 B2 | 4/2005 | Hughes | |
| 6,878,283 B2 | 4/2005 | Thompson | |
| 6,878,285 B2 | 4/2005 | Hughes | |
| 6,960,179 B2 | 11/2005 | Gura | |
| 7,033,498 B2 | 4/2006 | Wong | |
| 7,101,519 B2 | 9/2006 | Wong | |
| 7,208,092 B2 | 4/2007 | Micheli | |
| 7,241,272 B2 | 7/2007 | Karoor | |
| 7,276,042 B2 | 10/2007 | Polaschegg | |
| 7,326,576 B2 | 2/2008 | Womble et al. | |
| 7,435,342 B2 | 10/2008 | Tsukamoto | |
| 7,488,447 B2 | 2/2009 | Sternby | |
| 7,537,688 B2 | 5/2009 | Tarumi | |
| 7,544,300 B2 | 6/2009 | Brugger | |
| 7,544,737 B2 | 6/2009 | Poss | |
| 7,563,240 B2 | 7/2009 | Gross | |
| 7,566,432 B2 | 7/2009 | Wong | |
| 7,597,806 B2 | 10/2009 | Uchi | |
| 7,776,210 B2 | 8/2010 | Rosenbaum | |
| 7,794,419 B2 | 9/2010 | Paolini | |
| 7,850,635 B2 | 12/2010 | Polaschegg | |
| 7,922,686 B2 | 4/2011 | Childers | |
| 7,922,911 B2 | 4/2011 | Micheli | |
| 7,947,179 B2 | 5/2011 | Rosenbaum | |
| 7,955,290 B2 | 6/2011 | Karoor | |
| 7,988,854 B2 | 8/2011 | Tsukamoto | |
| 8,002,726 B2 | 8/2011 | Karoor | |
| 8,012,118 B2 | 9/2011 | Curtin | |
| 8,029,454 B2 | 10/2011 | Kelly | |
| 8,066,658 B2 | 11/2011 | Karoor | |
| 8,080,161 B2 | 12/2011 | Ding et al. | |
| 8,087,303 B2 | 1/2012 | Beavis | |
| 8,096,969 B2 | 1/2012 | Roberts | |
| 8,180,574 B2 | 5/2012 | Lo | |
| 8,187,250 B2 | 5/2012 | Roberts | |
| 8,197,439 B2 | 6/2012 | Wang | |
| 8,303,532 B2 | 11/2012 | Hamada | |
| 8,404,491 B2 | 3/2013 | Li | |
| 8,409,444 B2 | 4/2013 | Wong | |
| 8,480,607 B2 | 7/2013 | Davies | |
| 8,647,506 B2 | 2/2014 | Wong | |
| 8,733,559 B2 | 5/2014 | Wong | |
| 8,764,981 B2 | 7/2014 | Ding | |
| 8,777,892 B2 | 7/2014 | Sandford | |
| 9,144,640 B2 | 9/2015 | Pudil | |
| 9,254,355 B2 | 2/2016 | Sandford | |
| 9,527,015 B2 | 12/2016 | Chau | |
| 2001/0007931 A1 | 7/2001 | Blatter | |
| 2001/0009756 A1 | 7/2001 | Hei et al. | |
| 2002/0112609 A1 | 8/2002 | Wong | |
| 2002/0117436 A1 | 8/2002 | Rajan | |
| 2003/0080059 A1 | 5/2003 | Peterson et al. | |
| 2003/0097086 A1 | 5/2003 | Gura | |
| 2003/0105435 A1 | 6/2003 | Taylor | |
| 2003/0113931 A1 | 6/2003 | Pan | |
| 2003/0114787 A1 | 6/2003 | Gura | |
| 2004/0019312 A1 | 1/2004 | Childers et al. | |
| 2004/0099593 A1 | 5/2004 | DePaolis | |
| 2004/0147900 A1 | 7/2004 | Polaschegg | |
| 2004/0168963 A1 | 9/2004 | King | |
| 2004/0257409 A1 | 12/2004 | Cheok | |
| 2005/0006296 A1 | 1/2005 | Sullivan | |
| 2005/0056592 A1 | 3/2005 | Braunger et al. | |
| 2005/0101901 A1 | 5/2005 | Gura | |
| 2005/0113796 A1 | 5/2005 | Taylor | |
| 2005/0150832 A1 | 7/2005 | Tsukamoto | |
| 2005/0274658 A1 | 12/2005 | Rosenbaum | |
| 2006/0037483 A1 | 2/2006 | Kief | |
| 2006/0241543 A1 | 10/2006 | Gura | |
| 2007/0007208 A1 | 1/2007 | Brugger et al. | |
| 2007/0179431 A1 | 8/2007 | Roberts et al. | |
| 2007/0213665 A1 | 9/2007 | Curtin et al. | |
| 2008/0006570 A1 | 1/2008 | Gura | |
| 2008/0011664 A1 | 1/2008 | Karoor | |
| 2008/0051696 A1 | 2/2008 | Curtin | |
| 2008/0053905 A9 | 3/2008 | Brugger et al. | |
| 2008/0217245 A1 | 9/2008 | Rambod | |
| 2009/0020471 A1 | 1/2009 | Tsukamoto | |
| 2009/0078636 A1 | 3/2009 | Uchi | |
| 2009/0101552 A1 | 4/2009 | Fulkerson | |
| 2009/0120864 A1 | 5/2009 | Fulkerson | |
| 2009/0216045 A1 | 8/2009 | Singh | |
| 2009/0266358 A1 | 10/2009 | Sacristan Rock | |
| 2010/0004588 A1 | 1/2010 | Yeh et al. | |
| 2010/0007838 A1 | 1/2010 | Fujimoto | |
| 2010/0078381 A1 | 4/2010 | Merchant | |
| 2010/0078387 A1 | 4/2010 | Wong | |
| 2010/0084330 A1 | 4/2010 | Wong | |
| 2010/0100027 A1 | 4/2010 | Schilthuizen et al. | |
| 2010/0101195 A1 | 4/2010 | Clements | |
| 2010/0102190 A1 | 4/2010 | Zhu et al. | |
| 2010/0114012 A1 | 5/2010 | Sandford et al. | |
| 2010/0217181 A1 | 8/2010 | Roberts et al. | |
| 2010/0224492 A1 | 9/2010 | Ding et al. | |
| 2010/0312172 A1 | 12/2010 | Hoffman | |
| 2010/0312174 A1 | 12/2010 | Hoffman | |
| 2010/0314314 A1 | 12/2010 | Ding | |
| 2011/0009798 A1 | 1/2011 | Kelly | |
| 2011/0017665 A1 | 1/2011 | Updyke | |
| 2011/0048949 A1 | 3/2011 | Ding et al. | |
| 2011/0079558 A1 | 4/2011 | Raimann | |
| 2011/0163034 A1 | 7/2011 | Castellarnau | |
| 2011/0171713 A1 | 7/2011 | Bluchel | |
| 2011/0184340 A1 | 7/2011 | Tan | |
| 2011/0272352 A1 | 11/2011 | Braig | |
| 2011/0297593 A1 | 12/2011 | Kelly | |
| 2012/0018377 A1 | 1/2012 | Tsukamoto | |
| 2012/0095402 A1 | 4/2012 | Lande | |
| 2012/0248017 A1 | 10/2012 | Beiriger | |
| 2012/0273354 A1 | 11/2012 | Orhan et al. | |
| 2013/0018095 A1 | 1/2013 | Vath | |
| 2013/0019179 A1 | 1/2013 | Zhao | |
| 2013/0027214 A1 | 1/2013 | Eng | |

(56) References Cited

U.S. PATENT DOCUMENTS

| | | |
|---|---|---|
| 2013/0028809 A1 | 1/2013 | Barton |
| 2013/0030356 A1 | 1/2013 | Ding |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0158588 A1 | 6/2014 | Pudil |
| 2014/0158623 A1 | 6/2014 | Pudil |
| 2014/0190885 A1 | 7/2014 | Meyer |
| 2014/0190891 A1* | 7/2014 | Lura ................. A61M 1/28 210/662 |
| 2014/0217028 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |

FOREIGN PATENT DOCUMENTS

| | | |
|---|---|---|
| CN | 104936633 | 9/2015 |
| CN | 105658326 A | 6/2016 |
| DE | 102011052188 | 1/2013 |
| EP | 0264695 | 4/1988 |
| EP | 711182 B1 | 6/2003 |
| EP | 1701752 A2 | 9/2006 |
| EP | 1991289 | 11/2008 |
| EP | 1592494 B1 | 6/2009 |
| EP | 2575827 A2 | 12/2010 |
| EP | 2576453 A2 | 12/2011 |
| EP | 2446908 | 5/2012 |
| EP | 1545652 B1 | 1/2013 |
| EP | 1345856 B1 | 3/2013 |
| EP | 2344220 B1 | 4/2013 |
| EP | 1345687 | 6/2013 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2013502987 | 10/2013 |
| WO | 9532010 A1 | 11/1995 |
| WO | 0057935 | 10/2000 |
| WO | 0185295 A2 | 11/2001 |
| WO | 2002043859 | 6/2002 |
| WO | 2003043677 A2 | 5/2003 |
| WO | 2003051422 A2 | 6/2003 |
| WO | 2004064616 A2 | 8/2004 |
| WO | 2004062710 A3 | 10/2004 |
| WO | WO 2005/062973 A3 | 7/2005 |
| WO | 2005123230 A2 | 12/2005 |
| WO | 2007089855 A2 | 8/2007 |
| WO | WO 20070103411 | 9/2007 |
| WO | 2008075951 A1 | 6/2008 |
| WO | 2009157877 A1 | 12/2009 |
| WO | 2009157878 A1 | 12/2009 |
| WO | 20090157877 | 12/2009 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | WO 2013/019179 | 2/2013 |
| WO | WO 2013/019994 | 2/2013 |
| WO | WO 2013/028809 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2015/080895 | 4/2015 |
| WO | WO 2015060914 | 4/2015 |
| WO | 2015142624 | 9/2015 |
| WO | 2015199764 | 12/2015 |
| WO | WO 2015-199863 | 12/2015 |
| WO | WO 2015-199864 | 12/2015 |
| WO | WO 2015199765 | 12/2015 |

OTHER PUBLICATIONS

U.S. Appl. No. 14/645,394_OA.
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL162] International Search Report from PCT/US2012/051946 dated Mar. 4, 2013.
[NPL163] U.S. Appl. No. 61/526,209.
[NPL1] PCT/US2014/065950 International Search Report and Written Opinion dated Feb. 24, 2015.
[NPL238] PCT Application, PCT/US20013/020404, filed Jan. 4, 2013.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.
[NPL244] U.S. Appl. No. 13/836,079, filed Mar. 15, 2013.
[NPL245] U.S. Appl. No. 14/240,129, filed Aug. 22, 2013.
[NPL247] U.S. Appl. No. 13/835,735, filed Mar. 15, 2013.
[NPL2] PCT/US2015/032492 International Search Report dated Nov. 19, 2015.
[NPL4] PCT/US2015/016270 International Search Report and Written Opinion dated Jun. 5, 2015.
[NPL518] Office Action in U.S. Appl. No. 14/269,589, dated Nov. 4, 2016.
[NPL519] Office Action in U.S. Appl. No. 13/586,824 dated Dec. 21, 2015.
[NPL520] Office Action in U.S. Appl. No. 13/586,824 dated Jun. 4, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL5] PCT/US2015/016273 International Search Report and Written Opinion dated Jun. 9, 2015.
[NPL681] PCT/US2015/020047 International Search Report and Written Opinion dated Jun. 29, 2015.
[NPL682] PCT/US2015/020047 International Preliminary Report on Patentability dated Jun. 30, 2015.
[NPL684] PCT/US2015/020044 Written Opinion dated Jun. 21, 2016.

(56) References Cited

OTHER PUBLICATIONS

[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL690] US2015/019881 International Search Report and Written Opinion dated Jun. 29, 2015.
[NPL692] PCT/US2014/065950 International Preliminary Report on Patentability dated Oct. 28, 2015.
[NPL6] PCT/US2015/032492 Written Opinion dated Nov. 19, 2015.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL7] PCT/US2015/020046 International Search Report and Written Opinion dated Jun. 29, 2015.
[NPL8] PCT/US2015/020044 International Search Report Written Opinion dated Jun. 30, 2015.
[NPL] European Search Report App 14865374.4, dated Jun. 12, 2017.
Chinese Office Action in App. No. 201580009563.X, dated Mar. 13, 2018.
European Search Report for App. No. 15812081.6, dated Mar. 8, 2018.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report in EP 15811454, dated Feb. 15, 2018.
European Search Report in EP 15812559.1, dated Jan. 31, 2018.
Office Action in Japanese Application No. 2016-553344, dated Apr. 24, 2018.

* cited by examiner

REPLENISHING UREASE IN DIALYSIS SYSTEMS USING A UREASE INTRODUCER

CROSS-REFERENCE TO RELATED APPLICATIONS

This application is a divisional of, which claims benefit of U.S. patent application Ser. No. 14/633,852, filed Feb. 27, 2015, and which claims priority to U.S. Provisional Patent Application No. 62/031,101 filed Jul. 30, 2014, and claims priority to U.S. Provisional Patent Application No. 62/077,167, the disclosures of each of the above-identified applications are hereby incorporated by reference in their entirety.

FIELD OF THE INVENTION

The invention relates to an apparatus and related method for replenishing urease in a urease containing module, section, or compartment of a sorbent cartridge. The urease in the sorbent cartridge can be replenished by using a urease introducer that delivers urease into the sorbent cartridge via a urease injection port, an opening on the sorbent cartridge such as a door, or a slideable tray. The sorbent cartridge can receive the urease in a section of the sorbent cartridge that can contain an adjustable amount of urease that can be added by the urease introducer in varying amounts as needed before, during, or after a dialysis session. The section can also contain alumina, silica, or a combination thereof, which can be used to immobilize urease. The alumina, silica, or combination thereof, can be recharged by the addition of new urease by using the urease introducer of the present invention. In addition to the section, the sorbent cartridge can also contain another section that contains other sorbent materials such as zirconium phosphate.

BACKGROUND

Urease is a water soluble enzyme used in dialysis to convert urea into ammonium ions and bicarbonate. Oftentimes, urease can be immobilized electrostatically or covalently on an alumina or silica substrate inside a sorbent cartridge that is designed to be connected to a dialysis system. However, conventional immobilization of urease has been associated with the disadvantages of low loading and leaching of urease that can result in low urease sufficiency in dialysis. Moreover, conventional sorbent dialysis systems cannot, replenish, i.e., provide additional or specified amounts of urease to the sorbent cartridge or dialysis system before, during, or after a dialysis session. The inability to control the amount of urease added or available for system use can be problematic because the amount of urease required for a particular dialysis session can vary. The amount of urease required for a dialysis session may depend on a number of factors such as patient weight, urea load, dialysis time, etc. resulting in different rates and amounts of urease required per session. Using more or less than the required amount of urease for a particular dialysis session can translate into increased expenditures and waste from unused or overused urease as well as other sorbent materials contained in the sorbent cartridge.

Known sorbent dialysis cartridges and systems further cannot measure the amount of urease used during a particular session or replenish or add urease back to the sorbent cartridge or system as needed should a session need additional quantities of urease, or should additional urease be needed in the case of faster fluid flow rates through the sorbent cartridge.

Sometimes, certain sorbent materials such as alumina and zirconium phosphate can be recharged such that the sorbent material is put back into a condition for use in sorbent dialysis. However, known systems cannot recharge some or all of the sorbent materials, some of which can be rechargeable components, within a sorbent cartridge that also contains urease without undesirable effects. For example, recharging zirconium phosphate in the same sorbent cartridge in which urease is immobilized on alumina or silica can result in urease being stripped off the alumina or silica. Known systems cannot therefore replenish urease lost due to the process of recharging zirconium phosphate or other non-water soluble, rechargeable sorbent materials inside the same cartridge, or add a specific amount of urease to a sorbent cartridge or sorbent system.

As such, there is a need for systems, methods, components and devices for optimizing use of sorbent materials such as urease within a sorbent cartridge. The need extends to systems that can replenish urease in a sorbent cartridge and related dialysis systems by either directly adding discrete amounts of urease or by continuously adding urease to the sorbent system by a delivery mechanism. The need includes a sorbent cartridge and related systems in which urease can be added on demand, continuously, and in specified, discrete amounts. The need extends to providing urease at a specified time such as after, before, or during a dialysis session. The need includes providing the urease while the system is operating or off-line. The need includes adding the desired amounts of urease in a simple and convenient manner in adjustable amounts. In general, the need can be broadly described as dynamically adding urease to sorbent cartridges and related dialysis systems. The need can include adjusting the amount of required urease depending on a measured amount of urea detected anywhere in the system or sorbent cartridge or other dialysis parameters.

There is also a need for a mechanism of directly adding urease to a sorbent cartridge, on demand. The need includes a way to inject urease into a sorbent cartridge or a part of a flow path anywhere upstream of the sorbent cartridge in the dialysis system by an easy-to-use delivery mechanism. There is also a need for a sorbent cartridge in which fresh urease can be added via a delivery mechanism to replenish or refill the urease in the sorbent cartridge. There is also a need for measuring an amount of urease required to be dynamically added to a sorbent cartridge depending on a measured amount of urea or a suitable indication of urea conversion known to those of ordinary skill. There is also a need for a sorbent cartridge having a section for containing urease wherein the section can contain an adjustable amount of urease. The need includes a sorbent cartridge optionally having a section for containing one or more sorbent materials in amounts that do not need to be adjusted.

There is a need for a system for adding or replacing urease either directly into the sorbent cartridge or by injecting urease into a delivery mechanism. There is a further need for a closed sorbent cartridge capable of receiving an adjustable amount of urease on demand, and a simple way to measure, replenish and/or refill urease during a dialysis session. The methods and systems require a way for introducing urease in continuous or specified and/or discrete amounts. The methods and systems may involve pre-set amounts of urease or dynamically adjustable amounts of urease. There is also a need for a system capable of replenishing urease that may be stripped out of the sorbent cartridge during maintenance or dialysis session.

SUMMARY OF THE INVENTION

The first aspect of the invention relates to a sorbent cartridge. In any embodiment of the first aspect of the invention, the sorbent cartridge can comprise a urease introducer for facilitating replenishment of urease to the sorbent cartridge.

In any embodiment of the first aspect of the invention, the urease introducer can be selected from any one of an injection port, a slideable tray, a door, and combinations thereof.

In any embodiment of the first aspect of the invention, the injection port can be sized to only introduce urease.

In any embodiment of the first aspect of the invention, the injection port can be in fluid communication with the sorbent cartridge and can have an optional valve for controlling fluid access into the sorbent cartridge.

In any embodiment of the first aspect of the invention, the injection port can be contained on an exterior sorbent cartridge section upstream from zirconium phosphate inside the sorbent cartridge, or can be in fluid connection with a fluid entry point of the sorbent cartridge.

In any embodiment of the first aspect of the invention, the slideable tray can be adapted to receive urease and can have an opening on a top and bottom side to allow for fluid flow.

In any embodiment of the first aspect of the invention, the slideable tray can be an annular ring hingeably disposed on the sorbent cartridge having an opened and closed position.

In any embodiment of the first aspect of the invention, the door can be hingeably disposed on an exterior side of the sorbent cartridge having an open and closed position to allow for access into an interior of the sorbent cartridge.

In any embodiment of the first aspect of the invention, the urease introduced through the urease introducer can be immobilized on a urease binding material selected from alumina, silica, or a combination thereof.

In any embodiment of the first aspect of the invention, the sorbent cartridge can contain urease and at least one or more sorbent materials. In any embodiment of the first aspect of the invention, the sorbent materials can be selected from the group consisting of activated carbon, hydrous zirconium oxide, ion exchange resin, zirconium phosphate, alumina, silica, and combinations thereof.

In any embodiment of the first aspect of the invention, the sorbent cartridge can comprise a first section for housing the at least one more sorbent material and a second section for housing the urease. The other sorbent materials can be housed in the first section, while alumina or silica can be separately housed in the second section, as described herein.

In any embodiment of the first aspect of the invention, the one or more sorbent materials can be either alumina, silica, or a combination thereof.

In any embodiment of the first aspect of the invention, the sorbent cartridge can be capable of being adapted to any part of a dialysis flow path. In any embodiment of the first aspect of the invention, the dialysis flow path can be a controlled compliant dialysis flow path.

In any embodiment of the first aspect of the invention, the second section can be adapted to receive the one or more sorbent material or a modular regeneration assembly containing the one or more rechargeable sorbent material.

In any embodiment of the first aspect of the invention, the urease introducer can be positioned upstream from zirconium phosphate inside the sorbent cartridge.

In any embodiment of the first aspect of the invention, the injection port can have a diameter sized to introduce urease at a flow rate for introducing urease into the sorbent cartridge.

In any embodiment of the first aspect of the invention, the injection port can be in fluid communication with the sorbent cartridge and can have an optional valve for controlling fluid access into the sorbent cartridge.

Any of the features disclosed as being part of the first aspect of the invention can be included in the first aspect of the invention, either alone or in combination.

The second aspect of the invention relates to a method that can comprise the steps of detecting an amount of urea or other known urea conversion parameter, converted by urease inside a sorbent cartridge to ammonia and/or carbon dioxide and supplying urease to the sorbent cartridge if the amount of urea converted by urease inside the sorbent cartridge to ammonia and/or carbon dioxide is insufficient, wherein the sorbent cartridge is adapted to receive an adjustable amount of urease.

In any embodiment of the second aspect of the invention, the step of detecting the amount of urea converted to ammonia and/or carbon dioxide can be performed by any one of the means selected from the group consisting of an optical sensor, a chemical sensor, a blood urea nitrogen assay, and combinations thereof.

In any embodiment of the second aspect of the invention, the step of supplying urease can be performed by introducing a urease solution with a concentration between any of 1 mg/mL to 250 mg/mL, 15 mg/mL to 150 mg/mL, 10 mg/mL to 100 mg/mL, or 75 mg/mL to 250 mg/mL of urease into the sorbent cartridge.

In any embodiment of the second aspect of the invention, the step of supplying urease can be performed by introducing between any of 1.3 mL to 13.3 mL, 1.5 mL to 3.5 mL, 2.3 mL to 10.3 mL, or 5.0 mL to 12.3 mL at an activity of 300 unit/mg of urease activity of a urease solution into the sorbent cartridge. In any embodiment of the second aspect of the invention, the step of supplying urease can be provided per session for any of the disclosed urease introduction ranges.

In any embodiment of the second aspect of the invention, the method can further comprise recharging one or more sorbent materials housed inside the sorbent cartridge by passing a solution containing an appropriate amount of solutes for recharging the one or more rechargeable sorbent materials through the sorbent cartridge.

In any embodiment of the second aspect of the invention, the method can further comprise recharging one or more sorbent materials housed inside the sorbent cartridge by replacing one or more modules of a modular regeneration assembly containing the amount of one or more rechargeable sorbent materials.

Any of the features disclosed as being part of the second aspect of the invention can be included in the second aspect of the invention, either alone or in combination.

DETAILED DESCRIPTION OF THE INVENTION

Figure 1:
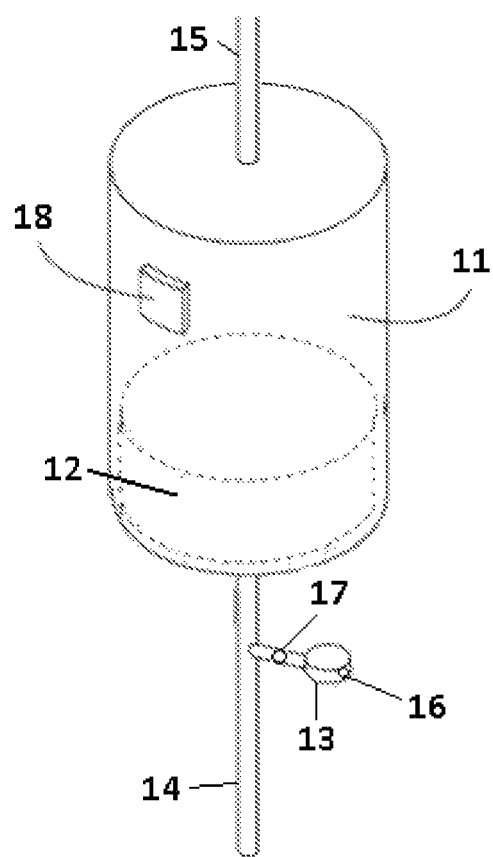
FIG. 1 is a perspective view of a sorbent cartridge having a urease injection port

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "adapted to receive" refers to a component wherein introduction of a substance into the component is possible.

An "adjustable amount" refers to an amount of a sorbent material that can be, but is not required to be, changed during a dialysis session.

An "ammonium sensor" is a sensor that is capable of detecting the presence of, or concentration of ammonium ions.

An "annular ring" is a ring having a substantially circular shape. The cross-section of the ring may be rectangular, triangular, round, or any other known shape. The ring may be constructed of any rigid or semi-rigid material, and may be adhered to the inner surface of a sorbent pouch by any means known in the art. An annular ring may also be an "o-ring."

The term "appropriate amount of solutes" refers to an amount of one or more solute(s) that is sufficient to accomplish a particular task. For example, an "appropriate amount of solutes" necessary to recharge the zirconium phosphate in a sorbent cartridge is the amount of sodium and hydrogen necessary to recharge the zirconium phosphate. The appropriate amount can be greater than the minimum amount necessary to accomplish the particular task.

A "blood urea nitrogen assay" is any analytical test that can determine the concentration of urea in blood or other fluids.

The term "cartridge" refers to any container designed to contain a powder, fluid, or gas made for ready connection to a device, structure, system, flow path or mechanism. The container can have one or more compartments. Instead of compartments, the container can also be comprised of a system of two or more modules connected together to form the cartridge wherein the two or more modules once formed can be connected to a device, structure, system, flow path or mechanism.

A "chemical sensor" is a sensor that senses one or more variables based on the chemical properties of a component of a medium.

A "compartment" means a part or a space designated, defined, marked or partitioned off from a structure. For example, a urease compartment in a sorbent cartridge is space defined within the sorbent cartridge containing urease. Optionally, the compartment can be in selected fluid communication with other compartments or modules of the sorbent system. The compartment can be physically separated or marked off without a physical barrier.

A "component" is any portion of a larger system. Non-limiting examples of components are containers, reservoirs, sensors, modules, and sorbents.

The term "comprising" includes, but is not limited to, whatever follows the word "comprising." Thus, use of the term indicates that the listed elements are required or mandatory but that other elements are optional and may or may not be present.

The term "configured to contain a sorbent material" refers to a component that is capable of holding a sorbent material. The component need not permanently hold the sorbent material in order to be configured to contain a sorbent material and can be of any size, configuration or geometry capable of retaining the sorbent material.

The term "consisting of" includes and is limited to whatever follows the phrase "consisting of" Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "contain" as used herein means to keep a material within a specific place. "Contain" can refer to materials that are placed within a compartment, absorbed onto a component, bound to a component, or any other method of keeping the material in a specific place.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. Generally, a container is a component of a larger system. A "sorbent container" is any receptacle configured to hold one or more sorbent materials. Similarly, a "urease container" is any receptacle configured to hold urease.

"Controlling fluid access" refers in one instance to a component that can be used to either allow fluid to access another component, or to not allow fluid to access another component. "Controlling fluid access" can also refer to a component that can be used to control the amount of fluid that can access another component.

"Cooperatively engaging" describes two compartments that have complementary engagement members that allow for an engagement configuration.

"Dialysate" is the fluid that passes through the dialyzer on the side of the dialysis membrane that is opposite to the fluid (e.g. blood) that is being dialyzed.

"Dialysis" is a type of filtration, or a process of selective diffusion through a membrane. Dialysis removes solutes in the blood of a specific range of molecular weights via diffusion through a membrane from a fluid to be dialyzed. During dialysis, a fluid to be dialyzed is passed on one side of a filter membrane, while dialysate is passed on the other side of that membrane. Dissolved solutes are transported across the filter membrane by diffusion between the fluids. The dialysate is used to remove solutes from the blood being dialyzed. The dialysate can also provide enrichment to the other fluid.

A "dialysis flow path" is the route in which a fluid will travel during dialysis.

"Engagement members" allow compartments to cooperatively engage. In certain embodiments, these engagement members may be clasps or latches.

An "exterior side" is a portion of a container or component that is on the outside of the container or component, as opposed to an "interior section" of a container or component, which denotes the inside of the container or component.

"Flow" refers to the movement of a fluid or gas.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The term "fluidly connectable" or "fluid connection" refers to the ability of providing for the passage of fluid or gas from one point to another point. The two points can be within or between any one or more of compartments, modules, systems, components, and rechargers, all of any type.

"Fluid entry point" refers to any point in a component or system that a fluid can be introduced to a portion of the component or system.

"Functional capacity" is the ability of a material to accomplish the material's intended function. In some instances functional capacity can refer to the ability of a sorbent material to remove specific solutes from a fluid, or to transform specific solutes into other materials.

"Hermetically sealed" refers to a seal that is airtight, or substantially impermeable to gases or fluids.

"Hingeably disposed" refers to a method of attachment wherein one component is connected to a second component by a hinge. The hinge allows for one component to turn or pivot while the other component is stationary.

"Immobilized," as used to refer to a chemical component, refers to a configuration wherein a chemical component is held in place by some force. The force may be provided by absorption, adsorption, adhesion, or any other method for the chemical to be held in place.

A "modular dialysate regeneration assembly" or "modular regeneration assembly" is one or more sorbent compartment containing at least one sorbent material attached to at least another sorbent compartment.

"Module" or "modular" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. The designation of "first," "second," "third," etc. does not refer to the respective placement of the module in the direction of fluid or gas flow, but merely serves to distinguish one module from another unless otherwise indicated.

"Multi-use" refers to a section of a sorbent cartridge that can be recharged, as used herein, such that after recharging, the sorbent cartridge can be placed back into service for dialysis. A multi-use section of a sorbent cartridge requires recharging of the sorbent materials within the sorbent cartridge, but not necessarily replenishment of the sorbent materials.

An "open" position is a configuration wherein the interior of a component is exposed to the surroundings. A "closed" position is a configuration wherein the interior of the component is cut off from the surroundings by a wall or other separator.

An "opening on the top side" or an "opening on the bottom side" refers to a passage for fluid on one side of a component.

An "optical sensor" is a sensor that senses one or more variables based on changes in the light emitted from, reflected from, absorbed by, or that travels through a medium.

The terms "pathway," "conveyance pathway," "fluid flow path," and "flow path" refer to the route through which a fluid or gas, such as dialysate or blood, travels.

"Recharging" refers to the process of treating a sorbent material to restore the functional capacity of the sorbent material, so as to put the sorbent material back into a condition for reuse or for use in a new dialysis session. In some instances, the total mass, weight and/or amount of "rechargeable" sorbent materials remain the same. In other embodiments, the total mass, weight and/or amount of "rechargeable" sorbent materials may change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease. Notably, urease is not generally "recharged," but can be replenished, as defined herein.

"Replenishing" means to add back into a system, section or module, a material that was previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" refers in one instance to a material that can be used more than one time, possibly with treatment or recharging of the material between uses. Reusable may also refer to a cartridge that contains a material that can be recharged by recharging the material(s) contained within the cartridge.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, but merely serves to distinguish one section from another unless otherwise indicated. Additionally, each section can be optionally physically separated such as by a divider or wall; however, referring to a particular section does not necessarily require physical separation and can merely refer to a particular location in which a material is contained.

A "sensor" is a component capable of determining the states of one or more variables in a system.

"Single-use" refers to a component, compartment, or module that is not capable of being recharged as defined herein. Oftentimes, a single use compartment can be replenished, as defined herein, with at least one material, e.g., urease, such that the compartment may be used in another dialysis session, but remains "single use" in the sense that the material is only being replenished, and not recharged.

When the single use compartment is no longer suitable for use in dialysis, the single use compartment may be discarded whereas a "rechargeable" compartment can be recharged and put back into operation.

"Sized to introduce urease" when referring to an injection port, refers to the size necessary for injecting the amount of urease needed for a dialysis session. Other materials may be possible to be injected into the injection port, but the size of the injection port is selected only based on the amount of urease necessary for a dialysis session.

"Solid urease" refers to urease in the solid phase of matter. The solid urease can be in a block of solid urease or in powdered form.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular dialysate regeneration assembly wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

"Sorbent materials" are materials capable of removing specific solutes from solution, such as urea or urea byproducts.

"Spent dialysate" is a dialysate contacted with blood through a dialysis membrane and contains one or more impurities, or waste species, or waste substances, such as urea.

"Upstream" of a section means positioned prior to that section in a fluid flow path. In normal operation, fluid will pass the "upstream" portion before passing the "downstream" portion.

The term "urease-binding sorbent material" refers to any material that can bind urease via any means including electrostatic, enzymatic, or intermolecular force binding of any kind.

The term "urease compartment" or "urease container" refers to a defined space or partition of any kind made from any material adapted for containing urease.

The term "urease door," or "door," refers to a portion of a component such as a sorbent cartridge that can be opened, and the contents of the sorbent cartridge behind the door can optionally be replaced.

The terms "urease injection port" or "injection port" refer to a temporary or non-temporary opening or passageway allowing for the entry of urease from one compartment to another.

The term "urease tray" refers to a drawer structure having a housing, generally being a sorbent cartridge, or alternatively the console of a sorbent dialysis cabinet, wherein the urease tray defines an interior volume defined therein that can be adapted to receive, for example, a urease pouch, module or loose sorbent material. The drawer can be "slideably movable," or a "slideable tray" with respect to the interior volume of the housing between a first closed position, wherein the compartments are enclosed within the interior volume, and a second open position, wherein the compartments are at least partially accessible. The "urease tray" can also optionally have a mechanism for controllably locking and/or sealing the drawer in the first closed position.

A "urease introducer" is any component of a sorbent cartridge that allows, facilitates, or provides for an amount of urease to be added to a sorbent cartridge. The use of the term introducer is used in the broadest sense. For example, the urease introducer can be an inlet, a flow passageway, a tube, a tray that functions to introduce urease into a defined compartment, or any other means that facilitates the introduction of urease.

A "urea sensor" is a component capable of detecting the presence of, or concentration of urea in a fluid.

The term "urease solution" refers to any aqueous solution being formulated by blending a solvent, such as a water based solvent, and urease. The solution can have optional components such as buffering components.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

Urease Injection System

The present invention provides for a sorbent cartridge containing all non-water soluble, rechargeable components inside a single compartment within, or contained separate from, the sorbent cartridge. The single compartment design contemplated by the first and second aspects of the invention can reduce fabrication and maintenance costs. In any embodiment of the first and second aspects of the invention, the non-water soluble, rechargeable components such as zirconium phosphate and alumina can be recharged. Any urease that is stripped off or required for operation can be added in a subsequent step back into the sorbent cartridge by the system or user. In this manner, the urease binding material such as alumina or silica in the sorbent cartridge can be replenished with urease. The sorbent cartridge of the first and second aspects of the invention includes re-filling or re-supplying, or otherwise adding an amount of urease back into the sorbent cartridge and related systems. In any such embodiment of the first and second aspects of the invention, urease can be provided by the urease introducer to replenish the available amount of urease present in the sorbent cartridge. As provided herein, the recharging of a sorbent material, such as alumina or zirconium phosphate, describes the ability to restore or enhance the functional capacity of the material. For example, alumina or zirconium phosphate can be recharged and restored to functional capacity by passing a solution containing the appropriate amount of solutes over the alumina or zirconium phosphate during a recharging process. Similarly, a rechargeable section or module can be recharged by passing the necessary solution through the section or module to restore the functional capacity of the module or section. In contrast, a replenishable sorbent material, in which its functional capacity has been reduced, is required to be replenished as described herein. Urease can be adsorbed by alumina, silica, or by combinations thereof wherein any such composition is rechargeable as defined herein.

In addition to introducing urease to a sorbent cartridge, the first and second aspects of the invention further allow an introduction of an amount of urease solution into any fluid flow path of a dialysis system. The fluid flow path can be appurtenant to a fluid entry point or inlet of a sorbent cartridge. The fluid flow path can also be any particular defined direction of fluid inside the sorbent cartridge. The urease solution can travel through the fluid flow path until the urease solution contacts any known urease binding material, such as alumina, silica, or a combination thereof, in a sorbent cartridge. The urease can then be adsorbed by the alumina, silica, or combination thereof, where the urease can stay for the duration of dialysis, thereby recharging the alumina, silica, or combination thereof. The urease can be immobilized or bound by any known means or material known by those of ordinary skill such as electrostatic or enzymatic binding. The urease can further be bound by any intermolecular interaction such as van der Waals forces. By adding fresh urease in this fashion, urease can be added to either open or closed sorbent systems. Providing urease via a urease introducer such as a urease injection port or tray, the sorbent cartridge can be shipped or stored without the urease present, while the urease can be added prior to, during, or after the sorbent cartridge is used. The adjustable aspect of urease introduction can reduce costs associated with the complexity and timing of manufacturing a sorbent cartridge containing urease. Notably, depending on such factors as the formulation and the storage state of the urease, the urease may have a limited shelf life. Moreover, the sorbent cartridge can be stored for long periods of time without problems to the viability of the urease by injecting the urease just prior to starting dialysis.

In particular, a sorbent cartridge can be replenished with fresh urease for each dialysis session wherein replenishing the urease in the sorbent cartridge can result in the recharging of other sorbent materials in the sorbent cartridge. For example, an alumina, silica substrate, or combinations thereof, which bind urease, in the sorbent cartridge, can be "recharged" and then "replenished" with fresh urease. Thereby, a single cartridge design with all non-water soluble components can be provided to simplify design and reduce cost per session wherein the urease can be re-introduced back into the sorbent cartridge whenever the amount of urease in the sorbent cartridge is reduced as additional functional capacity is needed.

The functional amount of the urease may be reduced in several ways: (1) the functional amount of urease may be reduced if the urease is stripped off of the sorbent cartridge due to the recharging of other sorbent materials, (2) by leaching out during dialysis, or during maintenance of the sorbent cartridge, or (3) by modification or rearrangement of the urease structure to make the urease less active.

One non-limiting embodiment of a sorbent cartridge of the first and second aspects of the invention with a urease injection port as the urease introducer is shown in FIG. 1. A first section of the sorbent cartridge can contain sorbent materials such as zirconium phosphate or zirconium oxide. A second section of the sorbent cartridge can be, for example, a sorbent module 11 that during operation can contain alumina, silica, or a combination thereof, and urease arranged as a layer, for example a urease and alumina or silica layer 12, or optionally, a urease layer (not shown). The urease can be bound to the alumina, silica, or combination thereof, layer covalently, electrostatically, by adsorption, or by any known methods or compositions. An additional layer of alumina, silica, or a combination thereof, not having any bound urease can be positioned after the urease/alumina or silica layer in the direction of fluid flow in order to reduce urease migration.

In any embodiment of the first and second aspects of the invention, the module 11 can comprise the entire sorbent cartridge with the other sorbent materials (not shown) arranged in the same module 11. In any embodiment of the first and second aspects of the invention, internal separators (not shown) can be placed within the sorbent modules to contain and physically separate the sorbent materials from each other. The separation can be formed as layers. Fluid can flow into the sorbent module 11 through inlet connector 14 and exit through outlet connector 15. The urease can be supported by the alumina, silica, or a combination thereof, which adsorbs the urease and keeps the urease within the sorbent module. A first section of the sorbent cartridge (not shown) can contain an amount of other sorbent materials. In any embodiment of the first and second aspects of the invention, one or more of the other sorbent materials can be recharged, such as zirconium phosphate. During recharging of the other sorbent materials, the urease can be stripped from the alumina, silica, or combination thereof, reducing the amount of urease in the sorbent module 11. Sorbent module 11 can be adapted to receive an amount of urease that can be adjusted as required based on specific parameters. The parameters can be related to a number of factors such as patient weight, urea load, dialysis time, etc. The parameters can result in different rates and amounts of urease required per session Once the amount of urease within the sorbent module 11 is reduced by the recharging process, or any other process that can reduce the amount of urease within the sorbent module 11, an amount of urease can be injected into the sorbent module 11 through the urease injection port 13 at injection site 16, and enter the urease and alumina, silica, or combination thereof layer 12. The urease injection port 13 can be in fluid communication with the sorbent module 11. The urease can be immobilized within the layer 12 where alumina, silica or a combination thereof within the sorbent module 11 can adsorb the urease, thereby recharging the alumina, silica, or combination of alumina or silica. In this way, the alumina, silica, or combination of alumina and silica, layer 12 can be permanently housed in the sorbent module 11, and a fresh amount of urease conveniently injected before each dialysis session. In any embodiment of the first and second aspects of the invention, the amount of urease added to the sorbent module can be varied depending on the blood urea nitrogen (BUN) levels and the size of the patient.

In any embodiment of the first and second aspects of the invention, the urease injected can be a solution of urease. The invention is adaptable to a wide range of fluids. The fluid of the solution can be water, buffer, priming solution, or any other fluid capable of dissolving the urease.

In any embodiment of the first and second aspects of the invention, other sorbent materials can be rechargeable. The urease injection system can allow for the sorbent cartridge to be a solid, fixed, structure. The sorbent materials, other than urease, can be recharged by passing a solution containing the appropriate amount of solutes through the sorbent cartridge. The urease, although removed during this process, can then be replenished by injecting new urease through the urease injection port. This allows the urease within the sorbent cartridge to be fully replenished, without the need to remove or disassemble the sorbent cartridge in order to refill the cartridge and respective modules or components with new urease. The non-water soluble sorbent materials can all be recharged by passing through the sorbent cartridge a solution containing the appropriate solutes, while the alumina, silica, or a combination thereof, can be recharged via the introduction of urease, which binds the alumina, silica, or a combination thereof, using the urease introduction system of the present invention. In any embodiment of the first and second aspects of the invention, the sorbent cartridge can be a single fixed, durable column that allows for recharging of all of the sorbent materials within the sorbent cartridge except for urease, and for addition of urease by injection into the column. In this way, the sorbent cartridge does not need to be replaced.

In any embodiment of the first and second aspects of the invention, a first section of the sorbent cartridge can be multi-use. That is, the sorbent materials within the first section of the sorbent cartridge can be recharged wherein the first section can be used multiple times without the need to replenish any of the materials. In contrast, a second section can be limited to single-use wherein once the second section is no longer suitable for dialysis, the second section can be discarded. However, the single use is not necessarily limited to a single dialysis session. For example, once an amount of a replenishable sorbent material inside the section, such as urease, has been reduced, the sorbent material, such as urease, can be replenished such that the single-use section is suitable for another dialysis session. The replenishment of urease does not render the second section into a multiple-use section because once the non-replenishable components, e.g. alumina are worn out, the single-use section should be discarded. In other words, the terms multi-use and single use refer to the components themselves, and not to the number of dialysis sessions that can be performed using the components or sections.

In any embodiment of the first and second aspects of the invention, an optional valve 17 can be placed downstream of the urease injection port 13. The valve 17 can control fluid access from the urease injection port 13 into the sorbent module 11. The valve 17 allows the system to control the amount of urease that can be injected into the sorbent cartridge, and also the timing of the urease injection.

In any embodiment of the first and second aspects of the invention, an optional urea detector 18 can be placed in the fluid flow path at some point after the alumina, silica, or combination thereof, and urease layer 12 of the sorbent module 11. A urea detector 18 can detect urea that has not been converted to ammonia and $CO_2$ by urease as described herein. The detection of ammonia may not be an indication of the sufficiency of insufficiency of urea conversion, but rather can indicate that the zirconium phosphate has reached functional capacity. Urea in the spent dialysate after being passed through a urease containing can indicate insufficient urease being present in the sorbent cartridge and that additional urease is required to be added to meet the therapy goals. Urea in the dialysate post-sorbent can signal a need to add more urease into the sorbent cartridge, or can signal that the prior urease addition did not work properly. In any embodiment of the first and second aspects of the invention, the system may give the user an audio or visual alert if the urea detector detects urea in the spent dialysate after passing through the urease containing module.

Figure 2:
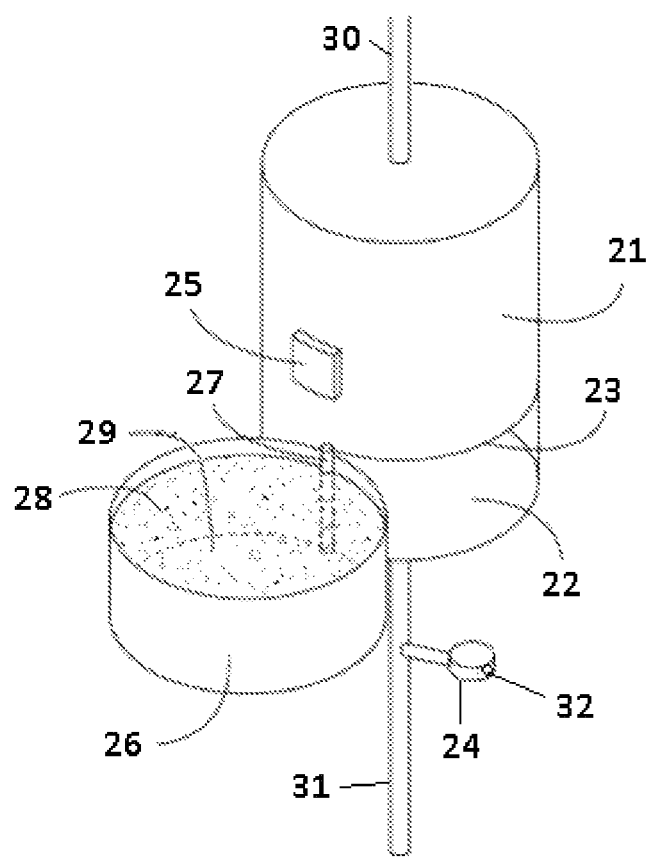
FIG. 2 is a perspective view of a sorbent cartridge having a urease introducer in the configuration of a urease tray.

In FIG. 2, the sorbent module 21 can be adapted to receive urease or alumina, silica, or a combination thereof, through a slideable urease tray 26. Fluid can enter the sorbent module 21 through inlet connector 31 and exit the sorbent module through outlet connector 30. An alumina, silica, or combination thereof, containing layer 28 may be removed through urease tray 26. A new alumina, silica, or combination thereof, containing layer 28 can then be placed into the urease tray 26 on top of the bottom portion 29 of the urease tray 26, and the urease tray 26 can slide back into the sorbent module 21. The alumina, silica, or combination thereof, in operation, will be in space 22. The alumina, silica, or combination of alumina and silica can be in a solid, fluid or powder form. The slideable urease tray 26 can have openings at the top and bottom (not shown) to allow fluid to pass through the slideable tray 26. In order to add the necessary urease back into the sorbent module 21, a urease solution can be injected into the urease injection port 24, fluidly connected to the sorbent module 21, and optionally positioned on the inlet connector 31, by injecting a urease solution through injection site 32. The urease injection port can be positioned so that the urease solution can be introduced on any part of the dialysis flow path prior to the position of the sorbent cartridge. The urease tray 26 can be connected to the sorbent module 21 in any fashion. For example, the urease tray 26 can be hingeably disposed on an exterior side of the sorbent module 21; connected to the sorbent module 21 by a hinge 27 at the side of the urease tray 26. In any embodiment of the first and second aspects of the invention, the urease tray 26 can be hermetically sealed to prevent contamination or leaking when in a closed position. A hermetic seal can be created with the use of PTFE sealing rings, o-rings, grease or any other material known in the art capable of creating a hermetic seal disposed on the edges of urease tray 26. In order to remove the alumina, silica, or combination of alumina and silica containing layer 28, the user can open the urease tray 26 by pivoting the urease tray 26 on the hinge 27, to place the urease tray 26 in an open position. In any embodiment of the first and second aspects of the invention, the urease tray 26 may have an engagement member (not shown) that can cooperatively engage the sorbent module 21 when closed and thereby resist inadvertent opening during use. In any embodiment of the first and second aspects of the invention, the urease tray 26 may be completely removable, and without any hinges (not shown). Engagement members (not shown) can be disposed on the edges of the urease tray 26 so that the user can remove the urease tray 26 from the sorbent module 21, but the urease tray 26 will not inadvertently disengage from the sorbent module 21. In any embodiment of the first and second aspects of the invention, the urease tray 26 can be an annular ring. That is, the urease tray 26 can be a circularly shaped tray around the sorbent module 21.

The urease, once injected, can travel in the fluid flow path until the urease contacts the alumina, silica or combination thereof, containing layer 28, where the urease can be adsorbed. This ensures that a fresh supply of urease is available. The urease addition can be controlled in this manner, ensuring that the urease is properly adsorbed by the alumina or silica and that none of the urease is wasted. The top of the alumina, silica, or combination thereof, layer space 23 can be covered by a material that restricts the flow of urease, thereby ensuring that the urease becomes adsorbed to the alumina or silica. As noted previously, another alumina, silica, or combination, thereof containing layer without bound urease can also be positioned after the alumina, silica, or combination thereof, and urease layer to prevent urease migration. Optional urea detector 25 can be placed in the fluid flow path after the urease and alumina or silica containing layer 28 to detect the presence of urea in the fluid after passing through the urease and alumina or silica containing layer 28.

In any embodiment of the sorbent cartridge of the first and second aspects of the invention, shown in FIG. 2, the alumina, silica, or combination of alumina and silica layer 28 can be in the form of a solid, dense material. In such embodiments of the first and second aspects of the invention, the urease tray 26 can be constructed without a bottom portion 29, and the alumina, silica, or combination of alumina and silica can be placed in the urease tray 26 without falling through the urease tray 26. In any embodiment of the first and second aspects of the invention, the sorbent module 21 can receive both of an amount of alumina, silica, or a combination thereof, and an amount of urease in the urease tray 26. In any embodiment of the first and second aspects of the invention, the urease tray 26 can be configured to contain an amount of solid urease. Optionally, the urease tray 26 can contain an amount of a sorbent material. The user can place the solid urease on the urease tray 26, so that when shut the solid urease is inside of the sorbent module 21. The solid urease can then be dissolved by fluid moving through the sorbent module 21 and be immobilized on any material that can immobilize urease known to those of ordinary skill. In any embodiment of the first and second aspects of the invention, the immobilizing material can be alumina, silica or a combination thereof, positioned inside the sorbent module 21.

Figure 3:
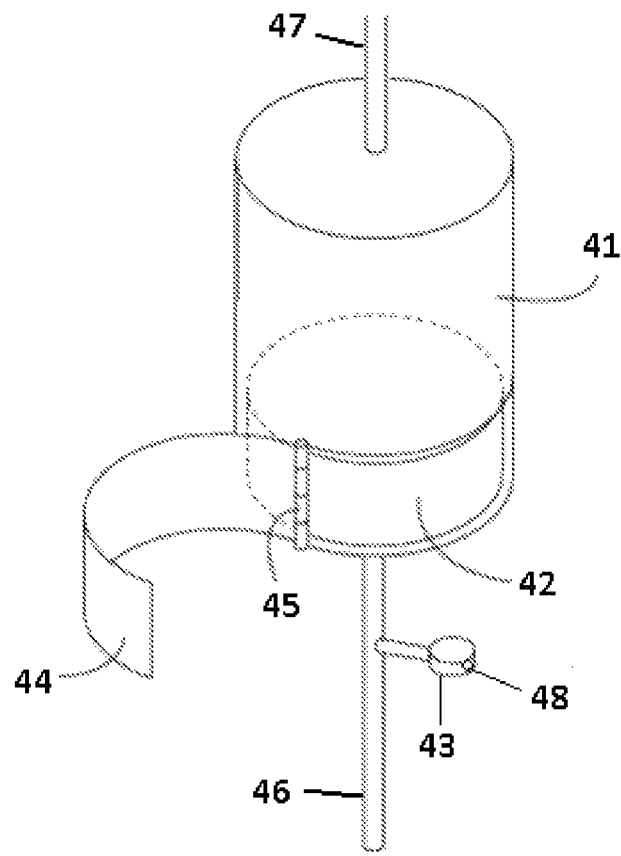
FIG. 3 is a perspective view of a sorbent cartridge having a urease introducer in the configuration of a urease door.

In FIG. 3, the alumina, silica, or combination thereof can be removed or inserted through urease door 44. The urease door 44 can be hingeably disposed on an exterior side of the sorbent cartridge 41 and can attach to the sorbent cartridge 41 by a hinge 45. Alumina, silica, or combination of alumina and silica layer 42 can be removed or inserted through the door when opened. An amount of urease can then be injected into an optional urease injection port 43 at injection site 48 in any amount required that can be adjusted depending on the dialysis conditions The urease can travel through inlet connector 46 to the alumina or silica layer 42. Fluid can exit the sorbent cartridge through outlet connector 47.

Figure 4:
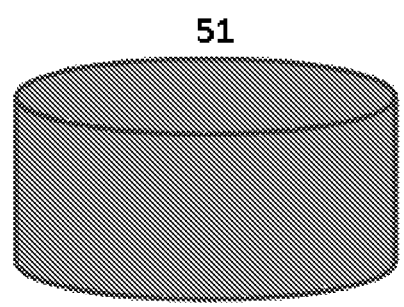
FIG. 4 is a perspective view of a disc containing alumina or silica and/or urease that can be introduced into a sorbent cartridge of the invention.

In any embodiment of the first and second aspects of the invention, as shown in FIG. 4, the alumina, silica or combination thereof, can be in the form of a solid cake 51. The solid cake of alumina, silica, or combination of alumina and silica 51 allows for the easy insertion and removal of alumina or silica from a sorbent cartridge. In any embodiment of the first and second aspects of the invention, the solid cake of alumina, silica, or combination of alumina and silica 51 can already have urease adsorbed onto the solid cake 51. In such embodiments of the first and second aspects of the invention, no urease injection port is necessary in the sorbent cartridge, and the urease introduction can be accomplished by adding the alumina or silica with adsorbed urease directly into the sorbent cartridge. A solid cake of alumina, silica, or a combination thereof 51 can be formed from powdered material by any means known in the art. In any embodiment of the first and second aspects of the invention, the powdered silica or alumina can be formed into a solid cake via compressing and extruding the material with fluid channels allowing fluid to leave the material. In any embodiment of the first and second aspects of the invention, the solid cake of alumina, silica, or a combination thereof, can be housed in a smaller preformed cartridge with rigid walls. The preformed cartridge can be inserted into the sorbent cartridge in the same manner as discussed for the solid cake of material.

In any embodiment of the first and second aspects of the invention, the urease injection port can be located at any position upstream of the layer containing alumina, silica or a combination thereof. In any embodiment of the first and second aspects of the invention, as shown in FIGS. 1-3, the urease injection port can be located in a fluid loop at a position located before the sorbent module.

Figure 5:
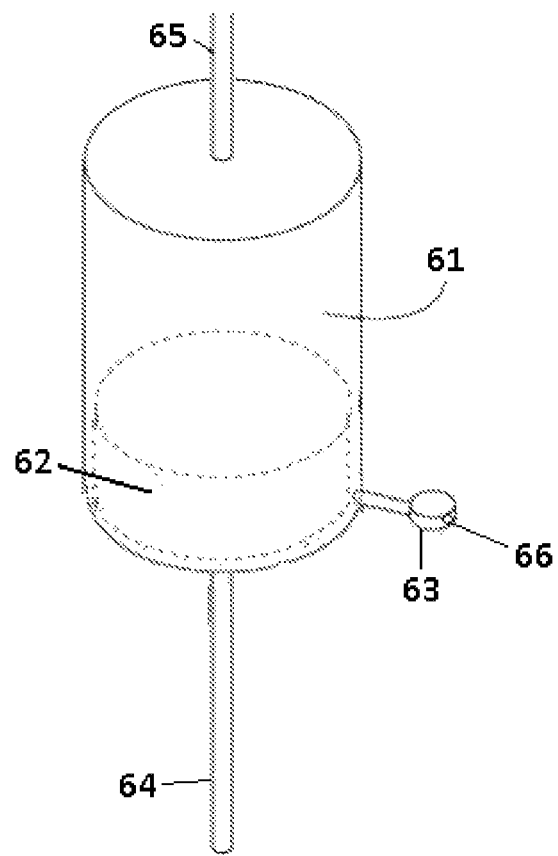
FIG. 5 is a perspective view of a sorbent cartridge having a urease injection port located directly on the sorbent cartridge.

In any embodiments of the first and second aspects of the invention, as shown in FIG. 5, the urease injection port 63 can be located directly on the sorbent module 61. The sorbent module 61 can contain an alumina, silica, or combination thereof, layer 62. Fresh urease can be added to the sorbent module 61 through urease injection port 63 by injecting a urease solution at injection site 66. The urease solution can enter the sorbent module 61 where the urease will be immobilized by adsorption onto the alumina, silica, or combination of alumina and silica layer 62. During dialysis, fluid can enter the sorbent module 61 at inlet connector 64, and exit at outlet connector 65.

Figure 6:
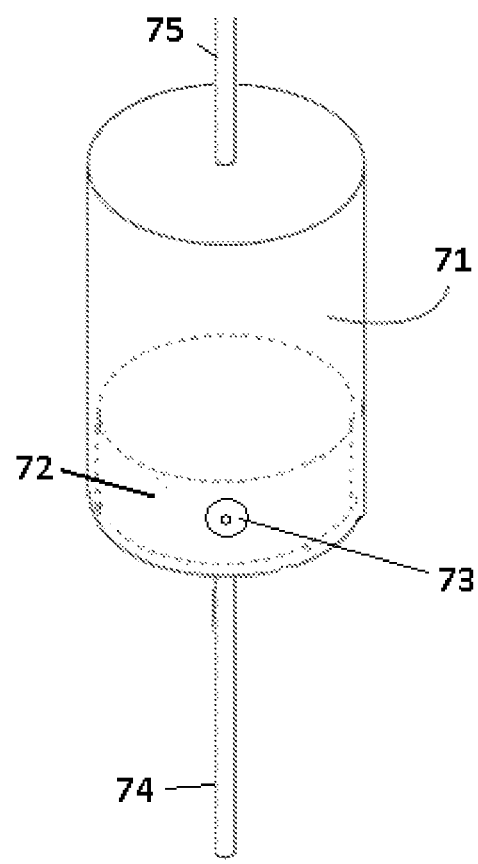
FIG. 6 is a perspective view of a sorbent cartridge with a pierceable septum for introducing urease.

FIG. 6 shows an embodiment of the first and second aspects of the invention with a pierceable septum instead of a urease injection port. The pierceable septum 73 can be located on a sorbent cartridge 71. A layer of alumina, silica, or a combination thereof 72 can be placed within the sorbent cartridge 71 to immobilize the urease. The user can inject a solution of urease directly through the pierceable septum 73, where the urease will be immobilized by the alumina, silica, or combination of alumina and silica 72 and be ready for use in dialysis. During use, dialysate can flow through the inlet connector 74, through the sorbent cartridge 71 and out through the outlet connector 75.

In any embodiment of the first and second aspects of the invention, a tube (not shown) can extend inwardly into the sorbent cartridge 71 from the pierceable septum 73. The tube can have multiple pores throughout, allowing some of the urease solution injected through the septum 73 to exit the tube into the alumina or silica layer 72 as the urease solution travels, ensuring an even distribution of urease through the alumina or silica layer 72. The pierceable septum 73 can be located in any position on the sorbent cartridge 71 provided that the pierceable septum 73 is at or upstream of the alumina or silica layer 72.

In any embodiment of the first and second aspects of the invention utilizing a urease injection port, any method of injecting the urease solution into the urease injection port is contemplated. For example, a user may fill a syringe with the urease solution and discharge the syringe into the urease injection port. The urease injection port may be covered by a septum, which can be pierced by the syringe. One of ordinary skill will appreciate that many types of injection ports can be used for the intended purpose of injecting urease. In any embodiment of the first and second aspects of the invention, the urease solution can simply be transferred by any suitable means into the urease injection port, and then pumped into the sorbent cartridge using a system of pumps and actuators. In such embodiments of the first and second aspects of the invention, the urease injection port may be covered with a removable cap that can be removed prior to addition of the urease solution. In any embodiment of the first and second aspects of the invention, the dialysis machine (not shown) can automatically inject the urease into the urease injection port. A urease solution can be provided for within the dialysis machine. Whenever the amount of urease within the sorbent cartridge is insufficient, the machine can automatically inject fresh urease into the urease injection port that travels to a binding layer within the system. The bound urease can then convert urea as needed.

Sodium chloride or sodium bicarbonate may be introduced into a sorbent cartridge in order to prime the sorbent cartridge for use. Similarly, citric acid may be introduced into the system after a dialysis session for disinfection. The amount of sodium chloride or sodium bicarbonate needed for priming, or the amount of citric acid needed for disinfection, can be significantly greater than the amount of urease needed for a dialysis session. In any embodiment of the first and second aspects of the invention, the urease injection port can be sized to introduce urease. That is, the urease injection port can have a suitable diameter for allowing fluid entry such that the diameter is too small to allow effective priming of the sorbent cartridge using the greater volumes and flow rates required during priming using sodium chloride and sodium bicarbonate. As such, the urease injection port can have a smaller diameter than a priming injection port sized to introduce sodium chloride and/or sodium bicarbonate for priming. The optimal size of the injection port whether for urease or priming fluid can be determined by fluid dynamics. Hence, one of ordinary skill in the art can determine a suitable diameter of a urease injection port that is sized specifically for the intended use of injection urease solution at a particular volume, concentration, flow rate and time. Possible benefits of a urease injection port having a specified diameter suitable for only urease solution injection are lowered manufacturing costs, tighter tolerances for allowing the injection port to fit into small areas, thus increasing design options of a dialysis system, and inherent safety check to ensure proper usage by an operator.

In any embodiment of the first and second aspects of the invention, the sorbent module can be part of a modular dialysate regeneration assembly. That is, other modules containing sorbent materials can be attached to each other. In any embodiment of the first and second aspects of the invention, the recharging of the sorbent materials in the module or modules that do not contain urease can be accomplished by simply replacing those modules. Dialysate regeneration refers to the process of treating spent dialysate, containing solutes removed from the patient's blood, with one or more sorbent materials in order to remove specific solutes, such as urea, and thereby generate dialysate that can be reused for dialysis.

The optional urea detectors described herein can be any detector capable of determining the presence of, or concentration of urea in the fluid after passing through the alumina or silica and urease layers. In any embodiment of the first and second aspects of the invention, the urea detectors can detect the amount of urea in the sorbent cartridge directly by measuring the amount of urea created by the breakdown of urea by the urease. Without being limited to any particular method, there are two general methods for the measurement of urea nitrogen. The diacetyl, or Fearon, reaction develops a yellow chromogen with urea, and this is quantified by photometry. The Fearon reaction has been modified for use in autoanalyzers and generally gives relatively accurate results. In the more specific enzymatic methods, the enzyme urease converts urea to ammonia and carbonic acid. These products, which are proportional to the concentration of urea in the sample, are assayed in a variety of systems, some of which are automated. One system checks the decrease in absorbance at 340 mm when the ammonia reacts with alpha-ketoglutaric acid. The Astra system measures the rate of increase in conductivity of the solution in which urea is hydrolyzed. The specimen should not be collected in tubes containing sodium fluoride because the fluoride inhibits urease. Also chloral hydrate and guanethidine have been observed to increase BUN values. Alternatively, urea can be measured indirectly by an ammonia detector located downstream of the urease layer and upstream of the zirconium phosphate layer. In general, low or no ammonia detected in fluid after passing through the urease layer but before reaching the zirconium phosphate layer may indicate that the zirconium phosphate has reached functional capacity.

In any embodiment of the first and second aspects of the invention, a urea detector can detect ammonia in the system that can indicate that zirconium phosphate contained within the system has reached functional capacity. In any embodiment of the first and second aspects of the invention, the amount of ammonia produced can be a function of the zirconium phosphate capacity and the system can determine if zirconium phosphate is required by the system.

Any method of detecting the amount of urea that is converted to ammonia in the sorbent cartridge is within the scope of the first and second aspects of the invention. In addition to the methods above, the detection can be accomplished by any means known in the art, including but not limited to, the use of an optical sensor, a chemical sensor, a blood urea nitrogen assay, an ammonium sensor, or any combination thereof. Urea in the fluid after the sorbent cartridge can be indicative of a lack of urease in the sorbent cartridge and fresh urease can be added.

In general, the sorbent cartridge of the first and second aspects of the invention can be adapted to receive an adjustable amount of urease. Any amount of urease may be injected or added as described herein in order to replenish the urease in the sorbent cartridge in adjustable amounts as required. Moreover, the addition can be done before, after or during dialysis. If the amount or level of urease in the sorbent cartridge or dialysis system becomes insufficient or lower than the required levels during dialysis, the adjustable nature of the addition allows for replenishment of urease in appropriate amounts without the need to stop dialysis. Critically, the adjustability of the amount of urease to be added in-session can provide flexibility in type of treatment delivered and therapy goals. The adjustable amount of urease can further provide for personalization of treatment and also result in a system that can be easily adapted to provide treatment for different patients. Adjustability in urease can reduce waste and tailor treatment to specific goals not possible with systems having not mechanism for adjusting an amount of urease being used during dialysis or across different treatment sessions.

Any usable concentration of urease within the urease solution to be added is within the scope of the first and second aspects of the invention. In any embodiment of the first and second aspects of the invention, the urease concentration can be between 10 mg/mL and 100 mg/mL. In any embodiment of the first and second aspects of the invention, the urease concentration can be between any of 1 mg/mL to 250 mg/mL, 15 mg/mL to 150 mg/mL, 10 mg/mL to 100 mg/mL, or 75 mg/mL to 250 mg/mL. In any embodiment of the first and second aspects of the invention having a urease concentration in the range from about 10 mg/ml to about 100 mg/ml, one non-limiting, preferred range for the injection volume can be 1.3 ml to 13.3 ml per session assuming 300 unit/mg of urease activity.

In any embodiment of the first and second aspects of the invention, the urease solution to be added can be provided in a pre-packaged amount. Before a dialysis session, whenever an amount of the urease within the urease module or urease pouch becomes reduced, or after recharging the other sorbent materials, between 1.3 mL and 13.3 mL of urease solution with an activity of 300 unit/mg can be added to ensure a fresh supply of urease within the sorbent cartridge. In any embodiment of the first and second aspects of the invention, the amount of urease solution added can be between any of 1.5 mL to 3.5 mL, 2.3 mL to 10.3 mL, or 5.0 mL to 12.3 mL or more.

In order to make use of the sorbent cartridge easier, and to enable use by non-trained users, such as patients, the urease can be provided in a separate sorbent container which contains the proper amount of urease to be added. A separate sorbent container containing a urease solution can ensure that the correct amount of urease is added to the sorbent cartridge, while avoiding waste by adding too much urease. In any embodiment of the first and second aspects of the invention, the amount of urease to be added can be based upon the needs of the patient. The amount of urease necessary for a dialysis session can depend on the blood urea nitrogen (BUN) content of the patient's blood. More urease can be added for patients with a higher BUN than for patients with a lower BUN. Heavier patients may also need more urease than patients that are lighter.

Before each dialysis session, after priming of the dialysis system, after a set number of dialysis sessions, whenever the amount of the urease within the module is reduced, or after each time the rest of the sorbent materials are recharged, the user would only need to inject the contents of the sorbent container into the urease injection port. In any embodiment of the first and second aspects of the invention, the system can prompt the user to inject a fresh urease solution into the sorbent cartridge before each dialysis session, after priming the dialysis system, after a set number of dialysis sessions, or after the other sorbent materials have been recharged. In embodiment of the first and second aspects of the invention, the urease solution injected into the urease injection port can be of a higher concentration. The urease injected can then be diluted by water as the water flows in the fluid flow path into the sorbent cartridge.

In order to test the effectiveness of urease solution injection for loading urease into a sorbent cartridge, such a with the urease injection port described herein, as opposed to loading urease to a column as a dry powder, several experiments were run. These experiments are described herein as Examples 1-4. Example 1 refers to the loading of urease onto a column using a dry powder loading procedure. Examples 2 and 3 are the analysis of the urease migration and urea conversion obtained from the dry powder loading procedure of Example 1. Example 4 relates to the loading and analysis of urease onto a column using a urease solution.

Example 1

An Ace Glass 25 millimeter Adjusta-Chrom Jacketed Column (P/N 5819) was packed with a mixture of 3.001 grams activated alumina (Shandong Luye Co, Lot 20140811-1) and 0.0040 grams of purified urease (Tokyo Chemical Industry, Lot P7DWG-TJ). An additional 9.0070 grams of activated alumina (Shandong Luye Co, Lot 20140811-1) was added to the column and the outlet frit and plunger were adjusted so that no dead space existed above the alumina layer and locked into place. Heated water was circulated through the external jacket of the column to maintain a temperature of 37° C. throughout the experiment. The column was primed by pumping base buffer (115 mMol sodium chloride and 25 mMol sodium bicarbonate) at 15 ml/minute until the liquid level reached the top of the alumina then held for five minute without flow to allow the urease to distribute and bind to the alumina. After the hold period the priming solution flow was restarted at 15 ml/min for an additional 5 minutes to complete the priming sequence. When the priming sequence was completed the column feed was changed to a test solution containing 25 mMol/Liter of urea (Sigma Aldrich) in base buffer. The flow rate was maintained at 15 mL/min for 60 minutes. The column effluent was collected for urease migration analysis and separate 8 mL samples were collected after 10, 30 and 60 minutes of test solution flow for urease conversion testing.

Example 2

A urea challenge solution was made containing 400 mMol/Liter phosphate buffer and 400 mMol/L urea. A 1.8 mL sample from the pooled column effluent from Example 1 was mixed with 1.8 mL of the urea challenge solution and incubated at room temperature for 10 minutes. Ammonium levels in the solution were measured using a Nova BioProfile 300 analyzer every 10 minutes over a period of 50 minutes. The ammonium concentration was plotted as a function of time and a linear regression was performed to determine the urease activity of the solution. The urease activity was then multiplied by the total volume of effluent run through the column to determine the total urease units (IU) that migrated during the test. For Example 1 the result was 53 International Units of migrated urease.

Example 3

The test samples collected at 10, 30 and 60 minutes in Example one were used for this analysis. A 0.8 mL aliquot of test sample was mixed with a 0.8 mL aliquot of 400 mM/L phosphate buffer and mixed vigorously. The ammonium concentration was determined using the Nova BioProfile 300 analyzer using the automated machine procedure. The results were compared to a standard curve measure in the same way using standard of known concentration. The ammonium concentration in the test sample is used to calculate the percent urea conversion for the urease/alumina reactor. For Example 1 the result was 53.4% urea conversion.

Example 4

The test system of Example 1 was modified to include a three way valve in the inlet feed line. The three way valve had one port compatible with a luer lock syringe and the other ports connected to the test solution and test column inlet. The Ace Glass 25 millimeter Adjusta-Chrom Jacketed Column was packed with 12.001 grams of alumina (Shandong Luye Co, Lot 20140811-1). A solution of 0.0079 grams urease (Tokyo Chemical Industry, Lot P7DWG-TJ) was mixed in 8.0 mL of base buffer (115 mMol sodium chloride and 25 mMol sodium bicarbonate) to make a solution of approximately 300 IU/mL. The urease was charged into the reactor by injecting 1.3 mL of base buffer, followed by 4.0 mL of urease solution and 1.8 mL of base buffer. The base buffer was used to fill the inlet line before introducing the urease and to ensure all the urease was flushed out of the inlet feed line and into the alumina. After introduction of the urease, the column was tested according to the method described in Examples 2-3. The urease migration for this test column was 47 International Units and the urea conversion was 67.4%.

The results of the experiments in Examples 1-4 are summarized in Table 1. As can be seen in Table 1, the results obtained from the urease solution loading were comparable to the results obtained with dry powder loading. The results demonstrate that a liquid load is possible without all of the enzyme migrating out of the column.

TABLE 1

| Method of Urease Loading | Urease Migration | Urea Conversion |
|---|---|---|
| Dry Powder Loading (Example 1) | 53 IU | 53.4% |
| Urease Solution Loading (Example 4) | 47 IU | 67.4% |

Sorbent Dialysis

Figure 7:
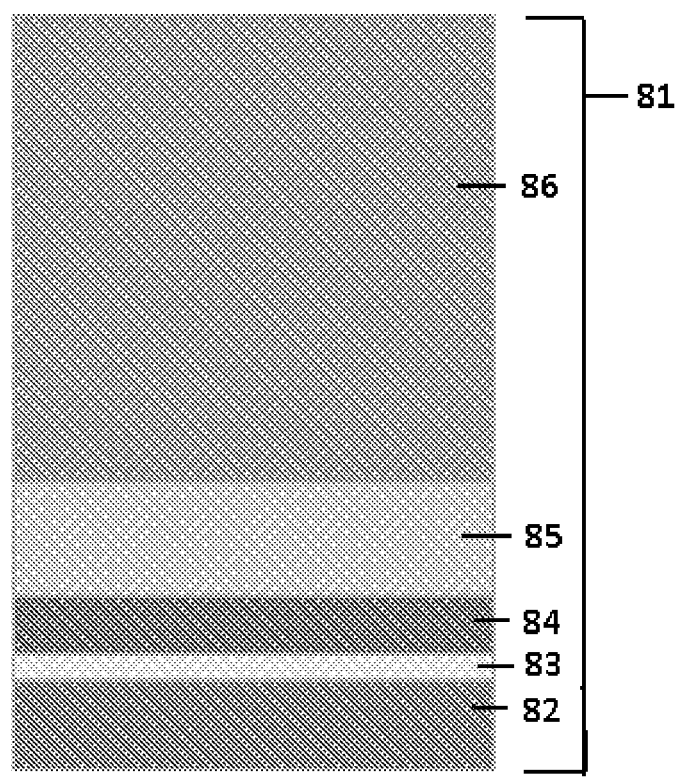
FIG. 7 an exemplary embodiment of a sorbent cartridge.

One non-limiting exemplary sorbent cartridge is shown in FIG. 7. Spent dialysate or fluid can flow from the bottom of the sorbent cartridge 81 to the top of the sorbent cartridge.

The first sorbent material the spent dialysate or fluid contacts can be activated carbon 82. Activated carbon 82 will remove nonionic toxins from the fluid by adsorption. Creatinine, glucose, uric acid, β2-microglobulin and other non-ionic toxins, except urea, can be adsorbed onto the activated carbon 82, removing those toxins from the fluid. Other non-ionic toxins will also be removed by the activated carbon 82. The dialysate or fluid then continues through the sorbent cartridge 81 into the alumina, silica, or combination thereof, and urease layer 83. The fluid can continue to move through the sorbent cartridge 81 into the hydrous zirconium oxide layer 84. The hydrous zirconium oxide layer 84 can remove phosphate and fluoride anions, exchanging them for acetate anions. Alternatively, layers 83 and 84 can be reversed wherein dialysate or fluid flows through the sorbent cartridge 81 first to a hydrous zirconium oxide layer now positioned at 83, and then continue to move through the sorbent cartridge 81 into the alumina or silica and urease layer now positioned at 84.

Urease can catalyze the reaction of urea to form ammonia and carbon dioxide. The result of this is the formation of ammonium carbonate. The phosphate anions present in the fluid can also be exchanged for hydroxide ions on the alumina or silica. As the fluid continues through the sorbent cartridge 81 in FIG. 7, the fluid reaches alumina, silica or combination thereof, layer 85. The layer of alumina, silica, or a combination thereof 85 can remove any remaining phosphate ions from the fluid and help retain urease within the sorbent cartridge 81, and in certain configurations this layer 85 can exchange urea for ammonium and other components. The last layer through which the fluid travels can be the zirconium phosphate layer 86. In the zirconium phosphate layer 86, ammonium, calcium, potassium and magnesium cations can be exchanged for sodium and hydrogen cations. Ammonium, calcium, potassium and magnesium ions all preferentially bind to the zirconium phosphate, releasing the hydrogen and sodium ions originally present in the zirconium phosphate layer 86. The ratio of sodium to hydrogen ions released depends on the ratio originally present in the zirconium phosphate layer 86, and is therefore controllable. The result of the fluid passing through the sorbent cartridge 81 is that the fluid can be regenerated and form clean dialysate that can be safely passed back through a dialyzer to a patient. In any embodiment of the first and second aspects of the invention, potassium, calcium, and magnesium can be added to the clean dialysate to replace any ions which were removed by the sorbent cartridge. The ions can be added and/or controlled via an infusate system that can be positioned on a section of the fluid flow path after the sorbent cartridge.

In any embodiment of the first and second aspects of the invention, the layers, 82, 83, 84, and 85 can comprise a first section of a sorbent cartridge that can be detached from a second section of the sorbent cartridge comprising layer 86 containing zirconium phosphate. The precise order of the layers of sorbent materials described in FIG. 7 is flexible, so long as zirconium phosphate is positioned downstream of the alumina or silica. In any embodiment of the first and second aspects of the invention, the sorbent materials within each section of the sorbent cartridge can be intermixed, as opposed to being arranged in layers.

In any embodiment of the first and second aspects of the invention, a layer of alumina, silica, or a combination thereof, can be placed upstream of the layer of activated carbon and downstream of the urease injection port. This ensures that portions of the urease injected into the sorbent cartridge are not removed from solution by the activated carbon prior to reaching the alumina or silica layer. In any embodiment of the first and second aspects of the invention, the alumina, silica, or combination thereof layer can be downstream of the layer of activated carbon. There is not a requirement that urease binds with alumina or silica in order to function properly. Urease can function in order to breakdown urea into ammonium and carbon dioxide, without the urease being bound to the alumina or silica. Importantly, because urease is water soluble, the urease should bind to some hydrophobic material within the cartridge so that the urease doesn't simply dissolve and pass through the cartridge. Alumina, silica, or a combination thereof, is generally used for this purpose, but any hydrophobic, non-water-soluble material could work for this purpose. In some cases, the urease can bind to the other sorbent materials within the cartridge, such as activated carbon, zirconium phosphate or zirconium oxide, without a reduction in urease activity. In any embodiment of the first and second aspects of the invention, the other sorbent materials, such as activated carbon, zirconium oxide or zirconium phosphate, can bind urease that migrates from the alumina or silica layer while the urease can remain active. In embodiments of the first and second aspects of the invention wherein the activated carbon layer is downstream of the layer of alumina, silica, or a combination thereof, the activated carbon can act as a safety backup, to capture urease that migrates through the alumina or silica and would otherwise leave the sorbent cartridge. In any embodiment of the first and second aspects of the invention, a carbon loaded filter pad with a pore size large enough to allow urease to pass through the filter can be placed upstream of the layer containing alumina, silica or a combination thereof. The carbon loaded filter pad can help to distribute the fluid flow through the cartridge, and remove trace contaminants in the starting water that could degrade the functionality of the urease. In any embodiment of the first and second aspects of the invention, the carbon loaded filter pad can have a pore size small enough to capture the urease.

The sorbent materials, other than urease, can be recharged by passing a fluid containing the correct solutes through the material. For example, zirconium phosphate can be recharged by passing a fluid containing hydrogen and sodium ions through the zirconium phosphate. The hydrogen and sodium ions will replace the ammonium, potassium, calcium, magnesium or other ions removed by the zirconium phosphate during dialysis, and thereby place the zirconium phosphate back in condition to be used in sorbent dialysis. Zirconium oxide can be recharged by passing a solution containing acetate ions through the zirconium oxide. The activated carbon can be recharged by passing heated water through the activated carbon. The amount of each of the solutions that must be passed through the respective sorbent materials depends on the amount of sorbent material used. As discussed herein, this process may strip the urease from the alumina or silica, necessitating replenishment of the urease.

One skilled in the art will understand that various combinations and/or modifications and variations can be made in the dialysis system depending upon the specific needs for operation. Moreover features illustrated or described as being part of an aspect of the invention may be included in the aspect of the invention, either alone or in combination.

We claim:
1. A method, comprising the steps of:
  detecting an amount of urea directly or indirectly by measuring products proportional to an amount of urea in a sample in a dialysate downstream of a sorbent cartridge; wherein the sorbent cartridge contains urease and at least one or more other sorbent materials; and supplying urease to the sorbent cartridge by a urease introducer if the amount of urea downstream of the sorbent cartridge is above a threshold, wherein the sorbent cartridge is adapted to receive an adjustable amount of urease, wherein the urease introducer comprises any one of a slideable tray and a door.

2. The method of claim 1, wherein the step of detecting the amount of urea in the dialysate downstream of the sorbent cartridge is performed by any one of the means selected from the group consisting of an optical sensor, a chemical sensor, a blood urea nitrogen assay, and combinations thereof.

3. The method of claim 1, wherein the step of supplying urease is performed by introducing a urease solution with a concentration between any of 1 mg/mL to 250 mg/mL, 15 mg/mL to 150 mg/mL, 10 mg/mL to 100 mg/mL, or 75 mg/mL to 250 mg/mL of urease into the sorbent cartridge.

4. The method of claim 1, wherein the step of supplying urease is performed by introducing between any of 1.3 mL to 13.3 mL, 1.5 mL to 3.5 mL, 2.3 mL to 10.3 mL, or 5.0 mL to 12.3 mL at an activity of 300 unit/mg of urease activity of a urease solution into the sorbent cartridge.

5. The method of claim 1, further comprising the step of:
recharging the at least one or more other sorbent materials housed inside the sorbent cartridge by passing a solution containing appropriate solutes for recharging the at least one or more other sorbent materials through the sorbent cartridge.

6. The method of claim 1, further comprising the step of:
recharging the at least one or more other sorbent materials housed inside the sorbent cartridge by replacing one or more modules of a modular regeneration assembly that make up the sorbent cartridge containing an amount of the at least one or more other sorbent materials.

7. The method of claim 5, wherein the step of supplying urease to the sorbent cartridge is performed after the step of recharging the at least one or more other sorbent materials.

8. The method of claim 1, wherein the step of supplying urease to the sorbent cartridge is performed during dialysis treatment.

9. The method of claim 1, wherein the step of supplying urease to the sorbent cartridge is performed prior to dialysis treatment.

10. The method of claim 1, wherein the step of supplying urease to the sorbent cartridge is performed after dialysis treatment.

11. The method of claim 1, wherein the step of supplying urease to the sorbent cartridge is performed by a dialysis system based on detection of urea in the dialysate downstream of the sorbent cartridge.

12. The method of claim 1, wherein an amount of urease introduced to the sorbent cartridge is based on one or more patient parameters.

13. The method of claim 12, wherein at least one of the one or more patient parameters is selected from the group consisting of: patient weight, a blood urea nitrogen content of the patient's blood, dialysis time, and urea load.

14. The method of claim 1, further comprising the step of injecting urease into the sorbent cartridge via a urease injection port.

15. The method of claim 14, wherein the urease injection port is located upstream of the sorbent cartridge.

16. The method of claim 14, wherein the urease injection port is located on the sorbent cartridge.

17. The method of claim 1, wherein the step of supplying urease to the sorbent cartridge further comprises the step of supplying alumina, silica, or a combination thereof by the slideable tray or door.

18. The method of claim 17, wherein the alumina, silica, or combination thereof includes urease adsorbed onto the alumina silica, or combination thereof.

19. The method of claim 1, wherein the step of supplying urease to the sorbent cartridge comprise supplying solid urease to the sorbent cartridge by the slideable tray or door.

20. The method of claim 19, wherein the sorbent cartridge comprises alumina, silica, or a combination thereof downstream of the slideable tray or door.

21. The method of claim 1, wherein the step of detecting an amount of urea indirectly is performed by measuring ammonia using an ammonia detector located downstream of a urease layer and upstream of a zirconium phosphate layer.

22. The method of claim 1, wherein the step of detecting an amount of urea indirectly is performed by measuring carbonic acid using a conductivity sensor measuring conductivity.

23. The method of claim 1, wherein the step of detecting an amount of urea indirectly is performed by measuring ammonia using photometry.

* * * * *